United States Patent [19]
Maruno et al.

[11] Patent Number: 6,165,378
[45] Date of Patent: Dec. 26, 2000

[54] POLYSACCHARIDE DERIVATIVE/ MAGNETIC METAL OXIDE COMPOSITE

[75] Inventors: Shigeo Maruno, Kani; Masakatsu Hasegawa; Takamasa Hanaichi, both of Nagoya; Katsutoshi Murase, Ama-gun; Hisato Yamada, Toyota; Hideo Nagae, Kasugai; Kyoji Kito, Nagoya, all of Japan

[73] Assignee: Meito Sangyo Kabushiki Kaisha, Aichi, Japan

[21] Appl. No.: 09/254,043

[22] PCT Filed: Aug. 28, 1997

[86] PCT No.: PCT/JP97/03009

§ 371 Date: Mar. 1, 1999

§ 102(e) Date: Mar. 1, 1999

[87] PCT Pub. No.: WO98/08899

PCT Pub. Date: Mar. 5, 1998

[30] Foreign Application Priority Data

Aug. 30, 1996 [JP] Japan ................................ 8246833

[51] Int. Cl.[7] .............................. C08L 5/00; C08K 3/08; C08B 37/00; A61K 49/06
[52] U.S. Cl. .................................... 252/62.53; 252/62.52; 252/62.54; 536/113; 536/121; 424/9.322; 424/9.364; 424/9.36; 424/493
[58] Field of Search ................................ 536/113, 121; 252/62.52, 62.53, 62.54; 424/9.322, 9.364, 9.36, 473

[56] References Cited

U.S. PATENT DOCUMENTS

| | | |
|---|---|---|
| 2,746,906 | 5/1956 | Novak et al. ........................ 167/95 |
| 2,876,165 | 3/1959 | Novak ................................. 167/92 |
| 3,480,555 | 11/1969 | Jackson et al. ..................... 252/62.56 |
| 4,101,435 | 7/1978 | Hasegawa et al. .................. 252/62.53 |
| 4,452,773 | 6/1984 | Molday ............................... 424/1.1 |
| 5,204,457 | 4/1993 | Maruno et al. ..................... 252/62.53 |
| 5,424,419 | 6/1995 | Hasegawa et al. .................. 532/113 |
| 5,739,304 | 4/1998 | Doenges et al. .................... 536/18.7 |
| 5,766,572 | 6/1998 | Hasegawa et al. .................. 424/9.322 |

FOREIGN PATENT DOCUMENTS

| | | |
|---|---|---|
| 59-30161 | 7/1984 | Japan . |
| 6-80588 | 3/1994 | Japan . |

OTHER PUBLICATIONS

K. Watanabe et al., Kogyo Kagaku Zasshi (*Japanese Journal of Industrial Chemistry*), 68, 1590 (1965).

W. McKernan et al., *Chemistry and Industry*, 11, 1490–1491 (1959).

*Primary Examiner*—C. Melissa Koslow
*Attorney, Agent, or Firm*—Wenderoth, Lind & Ponack, L.L.P.

[57] ABSTRACT

The present invention provides a polysaccharide-magnetic metal oxide complex consisting of a polysaccharide derivative obtained by carboxyalkyl-etherifying and unsubstituted or substituted aminoalkyl-etherifying a polysaccharide (the above carboxy group and/or amino group may be of a salt form) and a magnetic metal oxide. The above complex has a slow blood clearance and a low toxicity and is useful as a nuclear magnetic resonance imaging contrast medium.

21 Claims, 4 Drawing Sheets

F I G. 3
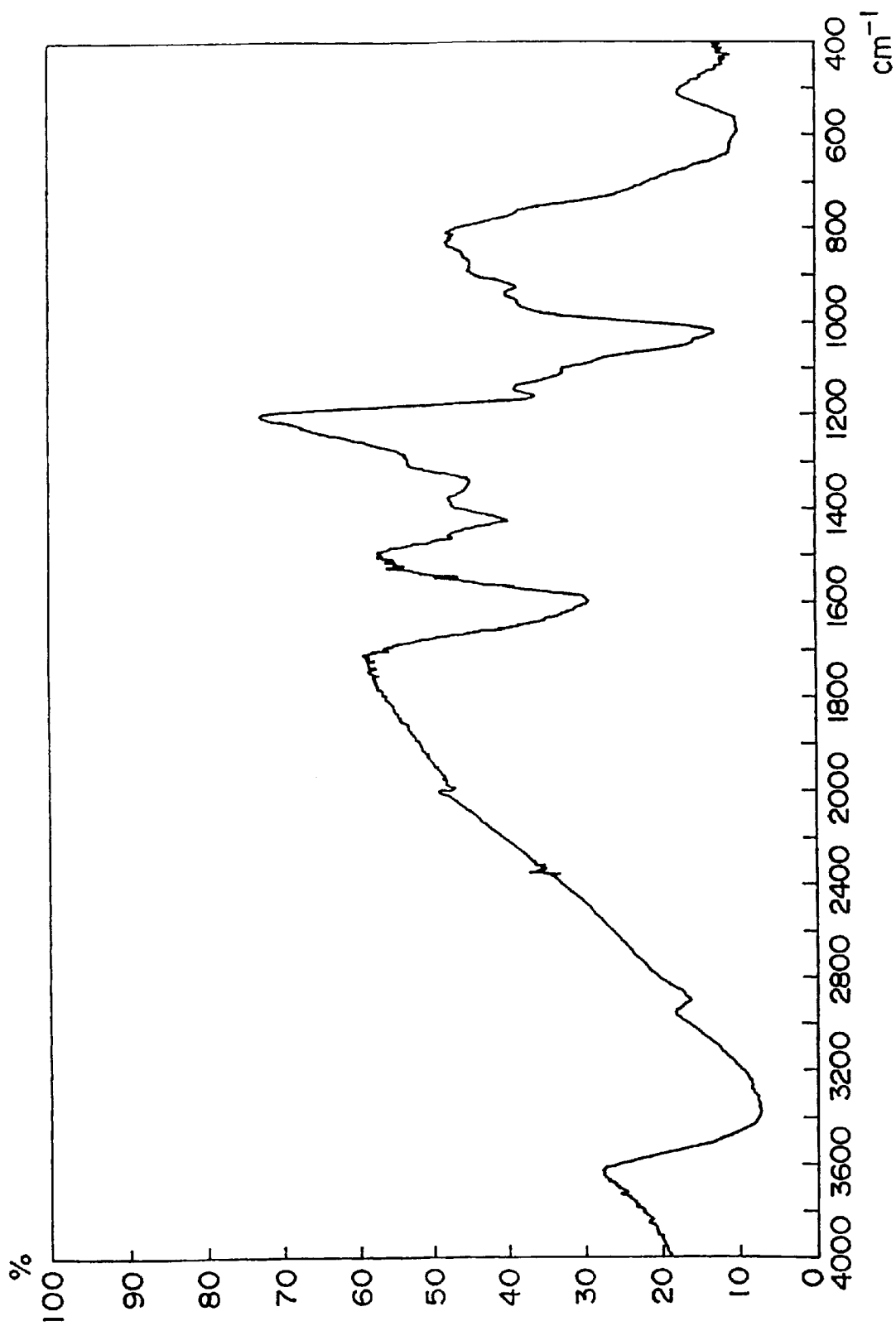

POLYSACCHARIDE DERIVATIVE/ MAGNETIC METAL OXIDE COMPOSITE

TECHNICAL FIELD

The present invention relates to a complex of a polysaccharide derivative which is substituted with both substituents of a carboxyalkyl group and an unsubstituted or substituted aminoalkyl group with a magnetic metal oxide, a production process for the same and a use thereof.

BACKGROUND ART

Complexes of polysaccharides or polysaccharide derivatives with magnetic metal oxides are proposed in order to improve stability and toxicity of aqueous magnetic sols. Disclosed in, for example, Japanese Patent Publication 13521/1984 (U.S. Pat. No. 4,101,435) are a complex of dextran or dextran modified with sodium hydroxide with magnetic iron oxide of a colloidal size and in U.S. Pat. No. 4,452,773, magnetic iron oxide microspheres obtained by covering magnetic iron oxide particles having a particle diameter of 10 to 20 nm with dextran. Further, complexes of carboxyalkyl ethers of polysaccharides with magnetic iron oxide having a particle diameter of 2 to 100 nm are disclosed in Japanese Patent Application Kokai (Laid-Open) 134001/1991 (U.S. Pat. No. 5,204,457). These complexes are useful as an MRI contrast medium, particularly an MRI contrast medium for liver but have several points to be improved in order to use them as an MRI contrast medium for other organs or sites.

Accordingly, the present investors have prepared a complex of a polysaccharide derivative having both substituents of a carboxyalkyl group and an unsubstituted or substituted aminoalkyl group with a magnetic metal oxide and administered it into a blood flow in the form of an aqueous sol to find that it has a slow blood clearance (slow removal from blood) and a low toxicity and is very useful as a nuclear magnetic resonance imaging (hereinafter abbreviated as MRI) contrast medium, particularly a contrast medium for a blood vessel, and thus have come to complete the present invention.

DISCLOSURE OF THE INVENTION

Thus, the present invention provides a complex of a polysaccharide derivative obtained by carboxyalkyl-etherifying or unsubstituted or substituted aminoalkyl-etherifying a polysaccharide (the above carboxy group and/or amino group may be of a salt form) with a magnetic metal oxide.

The complex of the present invention shall be explained below in further details.

The polysaccharide derivative (hereinafter referred to merely as a polysaccharide ether derivative) having both substituents of a carboxyalkyl ether group and an unsubstituted or substituted aminoalkyl ether group (the above carboxy group and/or amino group may be of a salt form, hereinafter the same) which is one component for constituting the complex of the present invention can be produced by carboxyalkyl-etherifying and an unsubstituted or substituted aminoalkyl-etherifying (hereinafter referred to as aminoalkyl-etherification) a polysaccharide by a method known per se. The order of carboxyalkyl-etherification and aminoalkyl-etherification shall not specifically be restricted, and from the viewpoint that the substitution rates of both substituents can easily be determined, the carboxyalkyl-etherification is preferably carried out first.

The carboxyalkyl-etherification of a polysaccharide can readily be carried out by, for example, adding an alkali to an aqueous solution or a suspension of the polysaccharide (this may be aminoalkyl-etherified in advance by the following method) and then adding monohaloalkylcarboxylic acid, particularly monochloroalkylcarboxylic acid to react them according to conventionally known methods, for example, methods described in U.S. Pat. No. 2,746,906, U.S. Pat. No. 2,876,165 and KOGYO KAGAKU ZASSHI (*Japanese Journal of Industrial Chemistry*) 68, 1590 (1965). Further, the aminoalkyl-etherification of a polysaccharide or a carboxyalkyl-etherified polysaccharide can be carried out as well by, for example, adding an alkali to an aqueous solution or a suspension of the polysaccharide or the carboxyalkyl-etherified polysaccharide and then adding unsubstituted or substituted aminoalkyl halide or corresponding epoxide, or unsubstituted or substituted ammonioalkyl halide or corresponding epoxide to react them according to methods known per se, for example, methods described in Chemistry and Industry, 1959, (11), 1490 to 1491 and Japanese Patent Publication 30161/1984.

A polysaccharide ether derivative having a desired intrinsic viscosity can be obtained by using a polysaccharide having a corresponding intrinsic viscosity for a starting material or preparing a polysaccharide ether derivative having a high viscosity in advance and then reducing the viscosity thereof. A neutral polysaccharide is preferred as the polysaccharide capable of being used as the starting material and include, for example, glucose polymers such as dextran, starch, glycogen, cellulose, pullulan, curdlan, schizophyllan, lentinan and pestalotian; fructose polymers such as inulin and levan; mannose polymers such as mannan; galactose polymers such as agarose and galactan; xylose polymers such as xylan, and L-arabinose polymers such as arabinan. Among them, dextran, starch, cellulose and pullulan are preferred, and dextran is particularly preferred. There can suitably used as the polysaccharide of the raw material, reduced polysaccharides obtained by reducing polysaccharides in advance by suitable reducing methods, for example, a method using sodium amalgam, a method using hydrogen gas in the presence of palladium carbon and a method using sodium boronhydride ($NaBH_4$).

Monohaloalkylcarboxylic acids capable of being used for the carboxyalkyl-etherification of the polysaccharide described above include particularly halolower alkylcarboxylic acids, for example, monochloroacetic acid, monobromoacetic acid, 3-chloropropionic acid, 3-bromopropionic acid, 4-chloro-n-butyric acid, 4-bromo-n-butyric acid, 2-chloropropionic acid and 3-chloro-n-butyric acid. The term lower used in the present specification means that a group or a compound having this term has 6 or less, preferably 4 or less carbon atoms. Thus, carboxyalkyl ethers of the polysaccharides suitable in the present invention include carboxymethyl ether, carboxyethyl ether and carboxypropyl ether. The carboxyl group of carboxyalkyl ether of the polysaccharide may have the form of a salt, and the salt thereof includes, for example, alkaline metal salts, amine salts and ammonium salts, preferably sodium salts.

Unsubstituted or substituted aminoalkyl halide or corresponding epoxide capable of being used for aminoalkyl-etherification of the polysaccharide (this may be carboxyalkyl-etherified in advance) includes, for example, a compound represented by the following formula:

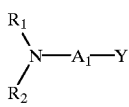

(I)

wherein

A₁ represents an alkylene group;

R₁ and R₂ represent independently a hydrogen atom or a hydrocarbon group (for example, alkyl, alkenyl, cycloalkyl, cycloalkenyl, cycloalkylalkyl, cycloalkenylalkyl, aryl and aralkyl) or R₁ and R₂ are combined with a nitrogen atom to which they are bonded to form a heterocyclic containing nitrogen (for example, aziridine, pyrrolidine, pyrroline, pyrone, pyrrole, piperidine, morpholine, indole, indoline and isoindoline); and Y represents a halogen atom or an epoxy group

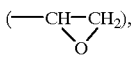

preferably a compound in which A₁ represents a lower alkylene group, and R₁ and R₂ represent independently a hydrogen atom or a lower alkyl group, or R₁ and R₂ are combined with a nitrogen atom to which they are bonded to form a 5- or 6-membered nitrogen-containing heterocyclic (for example, pyrrolidine, pyrroline, piperidine and morpholine). To be specific, included are, for example, aminomethyl chloride, aminomethyl bromide, aminoethyl chloride, aminopropyl bromide, methylaminomethyl chloride, methylaminomethyl bromide, ethylaminoethyl chloride, ethylaminoethyl bromide, ethylaminopropyl chloride, propylaminopropyl chloride, dimethylaminomethyl chloride, dimethylaminoethyl chloride, diethylaminomethyl chloride, diethylaminoethyl chloride, diethylaminoethyl bromide, diethylaminopropyl chloride, dipropylaminoethyl bromide, dipropylaminopropyl chloride, 1-pyrrolidinylmethyl chloride, 2-(1-pyrrolidinyl)ethyl chloride, 3-(1-pyrrolidinyl)propyl chloride, 1-piperidinylmethyl chloride, 2-(1-piperidinyl)ethyl chloride, 3-(1-piperidinyl)propyl chloride, and corresponding epoxides thereof.

An unsubstituted or substituted ammonioalkyl halide or a corresponding epoxide capable of being used for aminoalkyl-etherification of a polysaccharide (this may be carboxyalkyl-etherified in advance) includes, for example, a compound represented by the following formula:

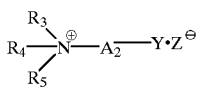

(II)

wherein

A₂ represents an alkylene group;

R₃, R₄ and R₅ represent independently a hydrogen atom or a hydrocarbon group (for example, alkyl, alkenyl, cycloalkyl, cycloalkenyl, cycloalkylalkyl, cycloalkenylalkyl, aryl and aralkyl), or at least two of R₃, R₄ and R₅ are combined with a nitrogen atom to which they are bonded to form a nitrogen-containing heterocyclic (for example, aziridine, pyrrolidine, pyrroline, pyrrole, piperidine, morpholine, pyridine and indole);

Y represents a halogen atom or an epoxy group

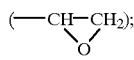

preferably a compound in which A₂ represents a lower alkylene group, and R₃, R₄ and R₅ represent independently a hydrogen atom or a lower alkyl group, or at least two of R₃, R₄ and R₅ are combined with a nitrogen atom to which they are bonded to form a 5- or 6-membered nitrogen-containing heterocyclic (for example, pyrrolidine, pyrroline, piperidine, morpholine and pyridine). To be specific, included are, for example, (described omitting the expression of the anion part) 2-chloroethyltrimethylammonium, 2-chloroethyltriethylammonium, 2-chloroethyltripropylammonium, 2-chloroethyltri-n-butylammonium, 3-chloropropyltrimethylammonium, 3-chloropropyltriethylammonium, 3-chloropropyltripropylammonium, 3-chloropropyltri-n-butylammonium, 3-chloro-2-hydroxypropyltrimethylammonium, 3-chloro-2-hydroxypropyltriethylammonium, 3-chloro-2-hydroxypropyltri-n-butylammonium, 3-chloro-2-hydroxypropyltri-iso-butylammonium, 3-bromo-2-hydroxypropyltrimethylammonium, 3-bromo-2-hydroxypropyltriethylammonium, 3-bromo-2-hydroxypropyltri-n-butylammonium, 3-bromo-2-hydroxypropyl-tri-iso-butylammonium, and corresponding epoxides thereof.

The use of the etherifying agent represented by the foregoing formula (I) or (II) described above can provide a polysaccharide ether derivative in which a hydroxy group of the polysaccharide is substituted with an aminoalkyl ether group represented by the following formula:

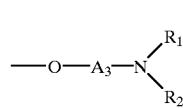

(III)

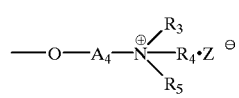

(IV)

wherein

A₃ and A₄ each represent an alkylene group which may be substituted with a hydroxy group, and R₁, R₂, R₃, R₄, R₅ and Z⁻ are synonymous with those defined above.

Suitable as the above aminoalkyl ether group is particularly a group represented by the following formula:

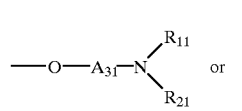

(III-1)

or

-continued

(IV-1)

wherein
- $A_{31}$ and $A_{41}$ each represent an alkylene group which may be substituted with a hydroxy group;
- $R_{11}$ and $R_{21}$ represent independently a hydrogen atom or a lower alkyl group, or $R_{11}$ and $R_{21}$ are combined with a nitrogen atom to which they are bonded to form a 5- or 6-membered nitrogen-containing heterocyclic;
- $R_{31}$, $R_{41}$ and $R_{51}$ represent independently a hydrogen atom or a lower alkyl group or at least two of $R_{31}$, $R_{41}$ and $R_{51}$ are combined with a nitrogen atom to which they are bonded to form a 5- or 6-membered nitrogen containing heterocycle; and
- Z represents an anion.

Particularly suitable aminoalkyl ethers of a polysaccharide include dimethylaminomethyl ether, diethylaminoethyl ether, dipropylaminopropyl ether, diethylaminopropyl ether, 2-(1-pyrrolidinyl)ethyl ether, trimethylammonioethyl ether, triethylammonioethyl ether, tripropylammonioethyl ether, trimethylammoniopropyl ether, triethylammoniopropyl ether, trimethylammonio-2-hydroxypropyl ether and triethylammonio-2-hydroxypropyl ether.

The unsubstituted or substituted amino group of the polysaccharide aminoalkyl ether can be present in the form of a salt, and not only acid-added salts but also ammonium salts represented by the formula (IV) or (IV-1) described above are included in the salt. The acid-added salts include inorganic acid salts such as, for example, hydrochloride, hydrofluoride, hydrobromide and nitrate; and organic acid salts such as, for example, formate and acetate.

The polysaccharide ether derivative containing an aminoalkyl ether group having the form of the ammonium salt represented by the formula (IV) or (IV-1) can be produced as well by using the compound represented by the formula (II) described above as the etherification agent or by etherifying the polysaccharide with the compound represented by the formula (I) described above and then reacting an amino group of an aminoalkyl ether group thereof with, for example, unsubstituted or substituted alkyl halide to thereby convert the amino group to the form of an ammonium salt.

Further, in the polysaccharide ether derivative having both substituents of a carboxyalkyl ether group and an aminoalkyl ether group, the carboxyl group and the amino group may form a salt in the molecule.

The polysaccharide ether derivative used in the present invention is preferably water-soluble, and the intrinsic viscosity thereof can fall generally in a range of about 0.02 to about 0.5 dl/g, preferably about 0.04 to about 0.2 dl/g and more preferably about 0.06 to about 0.1 dl/g.

The substitution rates of both substituents of the polysaccharide ether derivative each fall generally in a range of about 1% to about 30%, particularly about 2% to about 16% and more particularly about 3% to about 10%, and the substitution rates of both substituents stay preferably in the same degree. To be specific, a difference between the substitution rates, that is, (the substitution rate of the aminoalkyl ether group)–(the substitution rate of the carboxyalkyl ether group) falls advantageously in a range of usually less than 4%, preferably about –1% to about 3% and more preferably about 0% to about 2%. In the present invention, the substitution rate means a substitution percentage of each substituent based on the whole hydroxyl groups of the polysaccharide.

In the present invention, the intrinsic viscosity and the substitution rates of both substituents of the polysaccharide ether derivative are values obtained when measured in the following manners.

Measuring method of intrinsic viscosity $[\eta]$:

Measured at 25° C. according to a method described in Viscosity Measurement Method, Item 35, General Tests, The Pharmacopoeia of Japan (Twelfth Edition, 1991). A solvent used in this case is a 1M salt aqueous solution comprising the same ions as the paired ions of both substituents of the polysaccharide ether derivative having the form of a salt, usually a 1M NaCl solution.

Measurement of substitution rate of carboxyalkyl ether group:

According to one method, the substitution rate of the carboxyalkyl ether group of the polysaccharide ether derivative can be determined by using a polysaccharide carboxyalkyl ether which is an intermediate before carrying out aminoalkyl etherification. That is, the salt of the polysaccharide carboxyalkyl ether is dissolved in water, and this solution is suitably diluted to prepare a measurement sample solution. The metal content is determined according to a method described in Atomic Absorption Spectrophotometry, Item 20, General Tests, The Pharmacopoeia of Japan (Twelfth Edition, 1991) based on a standard sample (known concentration) of metal ions which are the paired ions of the carboxyl group of the sample solution, whereby the substitution rate of the polysaccharide carboxyalkyl ether is calculated.

The substitution rate of the carboxyalkyl ether group of the polysaccharide ether derivative can be measured as well by an infrared absorption method. That is, the substitution rates of the polysaccharide carboxyalkyl ether samples prepared by varying variously the substitution rate of the carboxyalkyl ether group are measured by the atomic absorption spectrophotometry described above, and the absorbances of the peaks in the vicinity of 1600 cm$^{-1}$ of the infrared absorption spectra of the samples described above are measured as well to prepare a standard curve drawn by plotting the substitution rates obtained by the atomic absorption spectrophotometry in relation to the absorbances of the peaks in the vicinity of 1600 cm$^{-1}$ of the infrared absorption spectra. Then, the absorbance of the peak in the vicinity of 1600 cm$^{-1}$ of the infrared absorption spectrum of 20 the polysaccharide ether derivative having an unknown substitution rate is read and applied to the standard curve described above, whereby the substitution rate of the above unknown sample can be determined.

Measurement of substitution rate of aminoalkyl ether group:

The nitrogen content of the polysaccharide ether derivative is measured according to a method described in Nitrogen Measurement Method, Item 30, General Tests, The Pharmacopoeia of Japan (Twelfth Edition, 1991) to calculate the substitution rate of the aminoalkyl ether group.

A ferromagnetic substance in which particles have a small diameter and therefore a size of a coercive force is small is used for the magnetic metal oxide which is the other component constituting the complex of the present invention.

Such magnetic metal oxide includes, for example, a compound represented by the following formula:

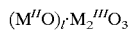  (V)

wherein $M^{II}$ represents a divalent metal atom;

$M^{III}$ represents a trivalent metal atom; and l is a real number in the range of 0 to 1.

In the formula (V) described above, the divalent metal atom $M^{II}$ includes, for example, magnesium, calcium, manganese, iron, nickel, cobalt, copper, zinc, strontium and barium. They can be used either alone or in combination of two or more kinds thereof. The trivalent metal atom $M^{III}$ includes, for example, aluminum, iron, yttrium, neodymium, samarium, europium and gadolinium. They can be used either alone or in combination of two or more kinds thereof.

Among the compounds represented by the formula (V) described above, the magnetic metal oxide in which $M^{III}$ is trivalent iron, that is, ferrite represented by the following formula is suitable:

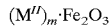  (V-1)

wherein $M^{II}$ is synonymous with what is described above, and m is a real number in the range of 0 to 1.

In this case, the same metal atoms as the examples shown in the formula (V) described above can be given for $M^{II}$. In particular, the magnetic metal oxide represented by the formula (V-1) in which M is divalent iron, that is, a magnetic iron oxide represented by the following formula can also be given as a magnetic metal oxide suitable in the present invention:

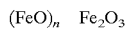  (V-2)

wherein n is a real number in the range of $0 \leq n \leq 1$.

In the formula (V-2) described above, when n is 0, the magnetic iron oxide is γ-iron oxide (γ-$Fe_2O_3$), and when n is 1, it is magnetite ($Fe_3O_4$). In the present invention, magnetic metal oxides having water of crystallization are included as well in the magnetic metal oxide.

As described above, the magnetic metal oxide can be a ferromagnetic substance and in general, it is to be described that the ferromagnetic substance has a magnetization in the range of about 1 to about 150 emu, preferably about 10 to about 150 emu and more preferably about 30 to about 150 emu per g of the metal at 25° C. in a magnetic field of 0.5 tesla (5000 oersted).

The magnetic metal oxide is reacted with the polysaccharide ether derivative described above usually in the form of a ultrafine particle. In general, magnetization of a magnetic substance particle is reduced in accordance with a reduction in the particle diameter, and such tendency becomes stronger when the particle diameter is 10 nm or less. Further, the coercive force of the magnetic metal oxide described above is reduced as well in accordance with a reduction in the particle diameter, and therefore the complex of the present invention has a small coercive force and is substantially superparamagnetic. The particle diameter of the magnetic metal oxide in the present invention can fall generally in the range of about 2 to about 20 nm, preferably about 3 to about 15 nm and more preferably about 3 to about 10 nm.

The complex of the polysaccharide ether derivative with the magnetic metal oxide according to the present invention can be produced by the following two roughly classified methods.

The first method is a method in which an aqueous sol containing particles of a magnetic metal oxide which is the core of the complex is prepared in advance and reacted with the above etherified product. The second method is a method in which a divalent metal salt, a trivalent metal salt and a base are mixed and reacted while stirring in the presence of the above etherified product in an aqueous system. These methods shall be explained below in further details.

In the first method, an aqueous sol (hereinafter referred to as a raw material sol) containing magnetic particles is first prepared, and this is reacted with a polysaccharide ether derivative to form a complex. The magnetic particles contained in the raw material sol have almost the same particle diameter and magnetism as those of the magnetic particles contained in the complex. Accordingly, it is desirable to prepare in advance the raw material sol containing magnetic particles having properties according to the objects. The raw material sol containing magnetic particles can be prepared by methods known per se. It can be prepared by, for example, an alkali coprecipitation method. To be specific, an aqueous solution containing, for example, a ferrous mineral acid salt and a ferric mineral acid salt in a ratio of about 1:3 to about 2:1 in terms of a mole ratio is mixed with a base such as NaOH, KOH and $NH_4OH$ so that the pH becomes 7 to 12, and the solution is heated and ripened, if necessary. Subsequently, magnetic iron oxide particles produced are separated and washed with water, followed by dispersing them again in water and adding mineral acid such as hydrochloric acid until the liquid reaches a pH of 1 to 3, whereby a magnetic iron oxide aqueous sol can be obtained. This aqueous sol can be refined and/or concentrated, if necessary, by dialysis, ultrafiltration and centrifugation. The magnetic iron oxide particles obtained by this method have a diameter falling usually in the range of about 5 to about 20 nm.

In the method described above, if a divalent metal salt is substituted for a part or all of the ferrous salt, a ferrite aqueous sol can be obtained in the same manner. The ferrite particles contained in the above sol have a diameter falling usually in the range of about 5 to about 20 nm. Examples of the usable divalent metal salt include mineral acid salts of metals such as magnesium, calcium, manganese, iron, nickel, cobalt, copper, zinc, strontium and barium. They may be used alone or in combination of plural kinds thereof.

Further, the raw material sol can be prepared as well by a method disclosed in Japanese Patent Publication 24663/1967 (U.S. Pat. No. 3,480,555). For example, an aqueous solution containing a ferrous salt and a ferric salt in a mole ratio of about 1:2 is added to a slurry of strong base ion exchange resins under stirring while maintaining the pH of the solution at 8 to 9, and then mineral acid such as hydrochloric acid is added until the pH becomes 1 to 3. Subsequently, the resins are filtered off, and the solution is refined and/or concentrated, if necessary, by dialysis, ultrafiltration and the like, whereby an aqueous sol of magnetic iron oxide is obtained. Magnetic iron oxide contained has a diameter falling usually in the range of about 5 to about 15 nm.

The raw material sol thus obtained can be mixed and reacted with an aqueous solution of the polysaccharide ether derivative to thereby prepare the complex. To be more specific, the polysaccharide ether derivative is reacted usually in a proportion of 1 to 10 parts by weight, preferably 3 to 5 parts by weight per one part by weight (in terms of metal(s)) of the magnetic particles contained in the raw material sol. The concentration of the magnetic particles contained in the reaction solution shall not specifically be restricted and can fall usually in the range of 0.1 to 10 w/vol %, preferably 1 to 5 w/vol % in terms of the metal(s). In general, the reaction can be carried out in the range of a room temperature to 120° C. for 10 minutes to 10 hours but, to be convenient, refluxing by heating for about one hour is enough. After cooling, refining and/or adjusting of the concentration can be carried out, if necessary. For example, a poor solvent for the complex such as methanol, ethanol, acetone and ethyl ether is added to the reaction solution thus obtained to precipitate and deposit the complex preferentially, and the deposit is separated, followed by dissolving the deposit again in water, dialyzing the resultant solution under flowing water and, if necessary, concentrating it under reduced pressure, whereby an aqueous sol of the complex having a desired purity and concentration can be obtained. Further, the aqueous sol of the complex having a desired purity and concentration can be obtained as well by repeating an operation to separate the unreacted ether compound and low molecular weight compounds from the complex formed by ultrafiltration. In this case, steps of pH adjustment, centrifugation and/or filtering can also be inserted, if desired, in the course and/or the final stage of the steps described above. The aqueous sol of the complex of the present invention thus obtained is dried by methods known per se, for example, preferably by freeze drying, whereby the complex of the present invention can be obtained as well in the form of powder.

The second method for producing the complex of the present invention is a method in which a mixed metal salt solution of a divalent metal mineral acid salt and a trivalent metal mineral acid salt is mixed and reacted with a base solution in an aqueous system in the pressence of the polysaccharide ether derivative to obtain the complex of the present invention by a single step. This second method can further be classified, according to the addition order, into (A) a method in which the mixed metal salt aqueous solution is added to an aqueous solution of the above etherified product, and then the aqueous base solution is added to carry out the reaction; (B) a method in which the aqueous base solution is added to the aqueous solution of the above etherified product, and then the mixed metal salt aqueous solution is added to carry out the reaction; (C) a method in which the aqueous solution of the above etherified product and the mixed metal salt aqueous solution are added to the aqueous base solution to carry out the reaction; and (D) a method in which a mixed solution of the aqueous base solution and the aqueous solution of the above etherified product is added to the mixed metal salt aqueous solution to carry out the reaction. These (A), (B), (C) and (D) methods are different only in the addition order and remain essentially unchanged in the other conditions. However, the method (A) is preferred in terms of being capable of changing widely at least the properties of the resultant complex.

In the preparation of the mixed metal salt aqueous solution described above, for example, when the divalent metal salt is a ferrous salt and the trivalent metal salt is a ferric salt, the ferrous salt and the ferric salt are dissolved in an aqueous medium in such a rate that the mole ratio of the ferrous salt to the ferric salt is about 1:4 to about 3:1, preferably about 1:3 to about 1:1. In this case, a part, for example, a half of the ferrous salt can be substituted with another divalent metal salt such as the salt of at least one metal selected from magnesium, calcium, manganese, iron, nickel, cobalt, copper, zinc, strontium and barium. The concentration of the mixed metal salt aqueous solution shall not specifically be restricted and suitably falls in the range of usually about 0.1 to about 3M, preferably about 0.5 to about 2M.

The metal salt includes, for example, a salt with at least one selected from mineral acids such as hydrochloric acid, sulfuric acid and nitric acid, usually hydrochloric acid. There can be used as the base, at least one selected from, for example, alkaline metal hydroxides such as NaOH and KOH; ammonia; and amines such as trimethylamine and triethylamine, usually NaOH. The concentration of the aqueous base solution can be changed over a wide range and falls suitably in the range of usually about 0.1 to about 10N, preferably about 1 to about 5N. The base is used in such an amount that the pH of the reaction solution after finishing addition becomes almost neutral to about 12, that is, the ratio of the metal salt to the base becomes about 1:1 to about 1:1.4 (normal ratio).

On the other hand, the polysaccharide ether derivative can be used in about 1 to about 15 times, preferably 3 to 10 times as much amount based on the weight of the metal contained in the metal salt used. The concentration of the polysaccharide ether derivative aqueous solution shall not strictly be restricted as well and falls suitably in the range of usually about 1 to about 30 w/vol %, preferably about 5 to about 20 w/vol %. The respective aqueous solutions can be added and mixed under non-heating or heating at about 0 to 100° C., preferably about 20 to about 80° C. while stirring. If necessary, a base or an acid is added to adjust the pH, and then the solution is refluxed by heating usually for about one hour, whereby the reaction can be carried out. The mixing and reaction described above can be carried out under an aerial atmosphere but can be carried out as well, if desired under an inert gas such as $N_2$ and Ar gases and a reducing gas such as $H_2$ gas or an oxidizing gas such as $O_2$ gas. The reaction solution thus obtained is refined in the same manner as in the first method described above and can be, if necessary, adjusted the pH, concentrated, filtered and dried. Magnetic metal oxide particles containing the resulting complex have a diameter falling in the range of usually about 2 to about 20 nm, preferably about 3 to about 15 nm and more preferably about 3 to about 10 nm.

Comparing the foregoing first and second methods for producing the complex of the present invention, the second method is preferred and generally practiced in terms of at least a length of the process and being capable of producing the complexes having various properties.

Further, the complex of the present invention can be produced as well by a method combining the first method with the second method, that is, a method comprising adding the polysaccharide ether derivative of the present invention to a pre-prepared known complex sol of polysaccharide or polysaccharide derivative with a magnetic metal oxide or a sol of known magnetic metal oxide microspheres coated with a polysaccharide (hereinafter called as a known magnetic complex sol) and, if necessary, heating for reaction, refining, adjusting the pH, concentrating, filtering and drying in the same manner as in the first method. In this case, there can be used, if necessary, a magnetic complex in which impurities and a free polysaccharide or polysaccharide derivative are reduced by refining a known magnetic complex sol by a known refining method, for example, reprecipitation by a poor solvent, gel filtration and ultrafiltration, and it is preferred. The method combining the first method with the second method and the magnetic complex obtained thereby are included as well in the present invention.

The ratio of the polysaccharide ether derivative to the magnetic metal oxide in the complex of the present invention depends on the diameter of the magnetic metal oxide particles and the molecular weight of the above etherified product and can be changed in a wide range. In general, the complex of the present invention can contain the polysaccharide ether derivative of about 0.2 to about 10 parts by weight, preferably about 0.5 to about 5 parts by weight and more preferably about 1 to about 3 parts by weight per part by weight of the metal contained in the magnetic metal oxide.

A metal content (this metal originates in the metal oxide contained in the complex) in the complex of the present invention is a value obtained when measured by the atomic absorption spectro photometry. That is, hydrochloric acid is added to the complex in the presence of a small amount of water to convert metal contained completely into chloride, and then, the resultant solution is suitably diluted and compared with the standard solution of each metal to determine the metal content.

Further, the content of the polysaccharide ether derivative contained in the complex is a value obtained when measured by a sulfuric acid-anthrone method according to Analytical Chem., 25, 1656 (1953). That is, a sulfuric acid-anthrone reagent is added to a solution obtained by suitably diluting the complex sol to develop color, and then the absorbance is measured. Subsequently, color is developed in the same manner using as a standard material the polysaccharide ether derivative used for producing the complex to measure the absorbance, and the content of the polysaccharide ether derivative contained in the complex is determined from the ratio of both absorbances.

The particle diameter of the magnetic metal oxide which is a component for the complex of the present invention is measured by X-ray diffraction. The freeze-dried complex powder of the present invention is subjected to X-ray diffraction by means of a powder X-ray diffractometer (target: Co, wavelength: 1.790 Å), and then several diffraction peaks corresponding to a specific compound can be observed. Accordingly, it can be found that the magnetic metal oxide (magnetic particles) contained in the complex is present in the form of crystal. The resultant diffraction peaks are broadened according to a reduction in the diameter of the magnetic particles contained in the complex, and therefore the diameter of the magnetic particles can be measured by X-ray diffraction. That is, with respect to the maximum peak in the X-ray diffraction, the particle diameter can be calculated according to the following Sherrer equation:

$$D = k\lambda/\beta \cdot \cos\theta$$

$$\beta = \sqrt{B^2 - b^2}$$

D: particle diameter (Å)
θ: Bragg angle (degree)
k: constant (0.9)
B: half band width (radian) of sample
λ: X-ray wavelength (1.790 Å)
b: half band width (radian) of standard sample The standard sample used is the same material having a particle diameter of 1 μm or more. The value thus obtained is relatively consistent with a value obtained by means of a transmission electron microscope.

Further, the diameter of the complex itself of the present invention is a value determined by a dynamic light scattering method (refer to, for example, Polymer J., 13, 1037 to 1043 (1981)), and the complex of the present invention can have a diameter falling in the range of usually about 10 to about 500 nm, preferably about 10 to about 100 nm and more preferably about 10 to about 50 nm.

The complex of the present invention is not merely a mixture and is a compound of the magnetic metal oxide particles with the polysaccharide ether derivative. This can be understood from, for example, the facts that addition of a poor solvent after finishing the reaction deposits preferentially the complex of the present invention and that when an aqueous sol of the complex of the present invention is fractionated, it can be separated into a complex containing sugar and metal and a free polysaccharide derivative.

$T_1$ and $T_2$ relaxivities (unit: 1/mM·sec) of the complex of the present invention having the form of an aqueous sol can be determined from a gradient of a straight line obtained by a least square method by measuring $T_1$ and $T_2$ relaxation times of aqueous sols obtained by diluting the complex of the present invention to various concentrations with water and water used for dilution by means of a pulse NMR of 20 MHz (the magnetic field is about 0.5 tesla), and here the above straight line is drove by plotting a relation of reciprocal numbers of the relaxation times thus obtained, that is, $1/T_1$ and $1/T_2$ (unit: 1/sec) with the metal contents (unit: mM) of the measured samples. The $T_1$ and $T_2$ relaxivities of the complex of the present invention having the form of an aqueous sol fall usually in the ranges of about 5 to about 100 $(mM \cdot sec)^{-1}$ and about 10 to about 500 $(mM \cdot sec)^{-1}$, preferably about 10 to about 50 $(mM \cdot sec)^{-1}$ and about 20 to about 300 $(mM \cdot sec)^{-1}$, respectively.

An acute toxicity $LD_{50}$ of the complex of the present invention having the form of an aqueous sol is about 15 to about 80 mmol/kg in terms of metal according to intravenous administration to mice and is identical to or less toxic than that of a complex obtained by using modified dextran. On the other hand, it is a little more toxic as compared with that of a complex obtained by using carboxyalkyldextran. That is, as shown in Test Example 1 which shall be described later, the complex of the present invention having a preferred embodiment, for example, the complex of complex No. 5 obtained in Example 1 had a $LD_{50}$ of 60 mmol (Fe)/kg. In general, the $LD_{50}$ of the complex of the present invention having a preferred embodiment is almost the same to about twice as compared with that of a complex synthesized in the same manner by using modified dextran and is almost the same to about half as compared with that of a complex synthesized in the same manner by using carboxyalkyldextran.

With respect to a speed (hereinafter referred to as blood clearance) at which the complex is removed from blood when the complex of the present invention having the form of an aqueous sol is intravenously administered, the complex of a preferred embodiment is very slowly removed as compared with the complex using modified dextran. That is, as shown in Test Example 2 which shall be described later, the blood clearances of the complexes of the present invention having a preferred embodiment, for example, the complexes of No. 5 and 6 obtained in Example 1 had half lives of 6.1 and 6.8 hours, respectively. In general, the blood clearance of the complex of the present invention having a preferred embodiment is slow by about twice to six times as compared with the complex using modified dextran or carboxyalkyldextran.

If the complex using modified dextran or carboxyalkyldextran is intravenously administered in the form of an aqueous sol, the complex is relatively quickly introduced into organs in which a reticuloendothelial system is advanced, for example, a liver and a spleen, and therefore the administered complex has a relatively fast blood clearance. On the other hand, when the complex of the present invention having a preferred embodiment is intravenously administered in the form of an aqueous sol, the above complex is scarcely introduced not only into organs of a reticuloendothelial system (liver, spleen, lung and bone) but also other organs (kidney cortex, kidney medulla, thymus gland, heart, small intestine and cerebrum), and therefore the blood clearance of the above complex becomes slow.

In addition, the complex of the present invention has a characteristic that by virtue of a lipophilic effect of the substituent of the polysaccharide ether derivative, it is liable to be introduced into sites which conventional complexes are hard to be introduced into, for example, lymph node, tumor and cancer sites.

Out of the complexes of the present invention, the complexes capable of becoming aqueous sols can be used as a so-called magnetic fluid for the industrial fields of mechanical sealant, magnetic clutch and magnetic ink. Preferably, it can safely be used in the biological and medical fields as, for example, an MRI contrast medium, particularly an MRI contrast medium for blood vessel or lymph node and an MRI contrast medium for tumor or cancer site and can be used for measurement of blood flow.

In the complex of the present invention capable of being preferably used as an MRI contrast medium, the polysaccharide ether derivative has an intrinsic viscosity falling preferably in the range of about 0.04 to about 0.2 dl/g, particularly about 0.06 to about 0.1 dl/g. The raw material polysaccharide is preferably dextran, starch, cellulose or pullulan, and the carboxyalkyl ether part of the polysaccharide ether derivative is suitably carboxymethyl ether, carboxyethyl ether or carboxypropyl ether, preferably carboxymethyl ether. The aminoalkyl ether part thereof is suitably diethylaminoethyl ether, dimethylaminomethyl ether, dipropylaminopropyl ether, trimethylammonio-2-hydroxypropyl ether, triethylammonio-2-hydroxypropyl ether and tripropylammonio-2-hydroxypropyl ether. Both substituents of the polysaccharide ether derivative have a substitution rate falling preferably in the range of about 2% to about 16%, particularly about 3% to about 10%, and both substituents have suitably almost the same substitution rates, to be specific, a difference between the substitution rates of both substituents, that is, (the substitution rate of aminoalkyl ether)–(the substitution rate of carboxyalkyl ether) falls suitably in the range of about –1% to about 3%, preferably about 0% to about 2%.

On the other hand, the magnetic metal oxide particle is preferably of magnetic iron oxide or ferrite, particularly magnetic iron oxide, and the magnetic particle has a diameter falling preferably in the range of about 3 to about 15 nm, particularly about 3 to about 10 nm. The complex itself has a diameter falling preferably in the range of about 10 to about 100 nm, particularly about 10 to about 50 nm. Further, the $T_1$ and $T_2$ relaxivities fall preferably in the ranges of about 5 to about 100 $(mM·sec)^{-1}$ and about 10 to about 500 $(mM·sec)^{-1}$, particularly about 10 to about 50 $(mM·sec)^{-1}$ and about 20 to about 300 $(mM·sec)^{-1}$, respectively.

When the complex of the present invention is used as an MRI contrast medium, the complex is used usually in the form of an aqueous sol. In this case, the concentration of the complex can be changed over a wide range and falls suitably in the range of about 1 mmol/L to about 4 mol/L, preferably about 0.1 mol/L to about 2 mol/L in terms of the metals. In preparing the aqueous sol, there can be added various physiologically allowable auxiliary agents such as, for example, inorganic salts such as sodium chloride; monosaccharides such as glucose, and sugar alcohols such as mannitol and sorbitol; organic acids such as acetic acid, lactic acid and citric acid; and a phosphate-buffered solution and a tris-buffered solution.

When the complex of the present invention is used as an MRI contrast medium, the dose thereof is different depending on purposes and can fall in a range of about 1 μmol/kg to about 10 mmol/kg, preferably about 2 μmol/kg to about 1 mmol/kg and more preferably about 5 μmol/kg to about 0.1 mmol/kg in terms of the metals. The administering method includes, for example, parenteral injection or infusion into a vein, an artery, a bladder, a lymph duct, muscle and subcutis but in a certain case, oral administration or direct enteric administration is possible as well.

BRIEF DESCRIPTION OF THE DRAWINGS

FIG. 3 is the infrared absorption spectral drawing (KBr method) of the freeze-dried powder of the complex No. 3 prepared in Comparative Example 2.

EXAMPLES

Figure 1:
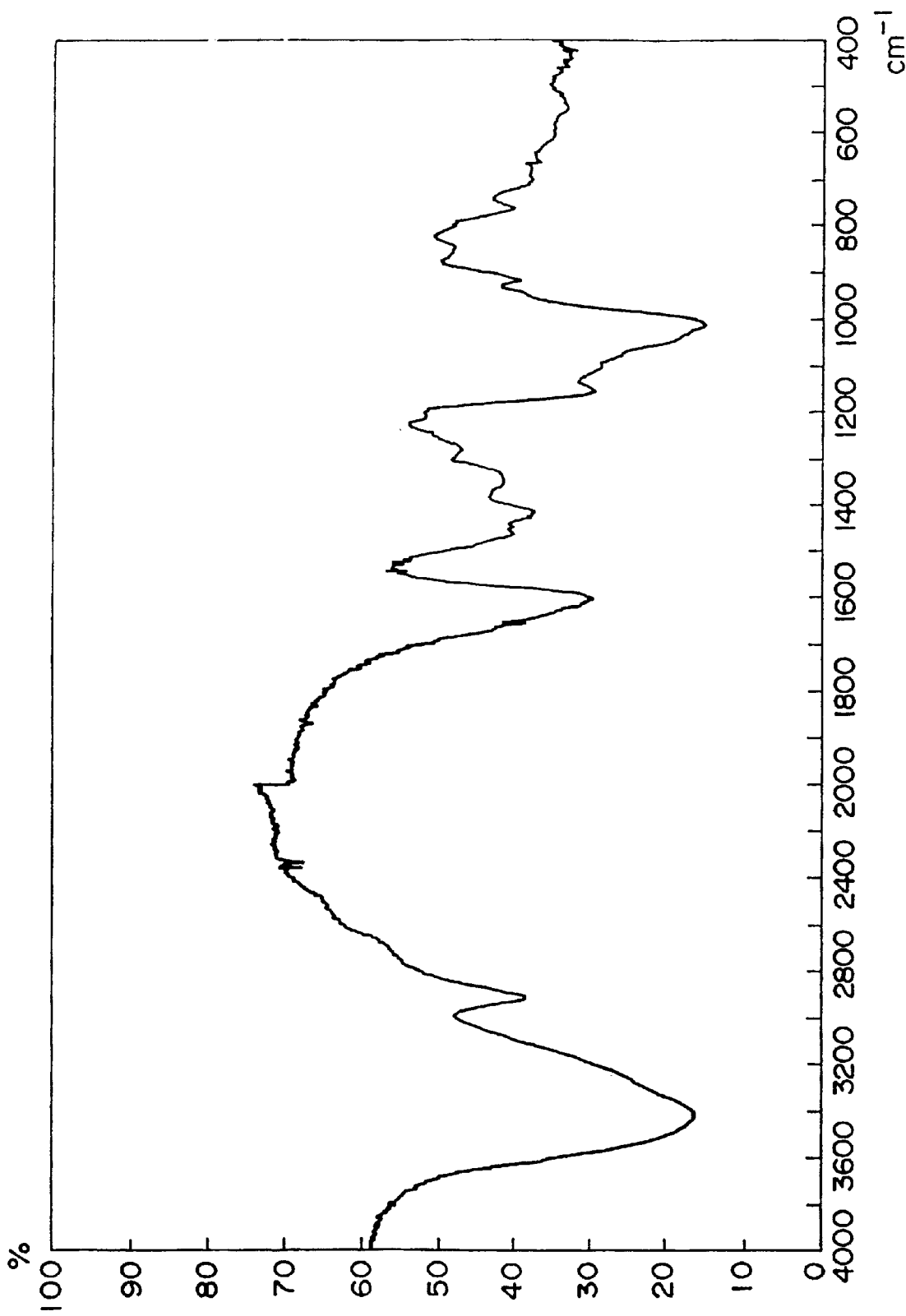
FIG. 1 is the infrared absorption spectral drawing (KBr method) of the polysaccharide derivative No. 3 prepared in Reference Example 1.
Figure 2:
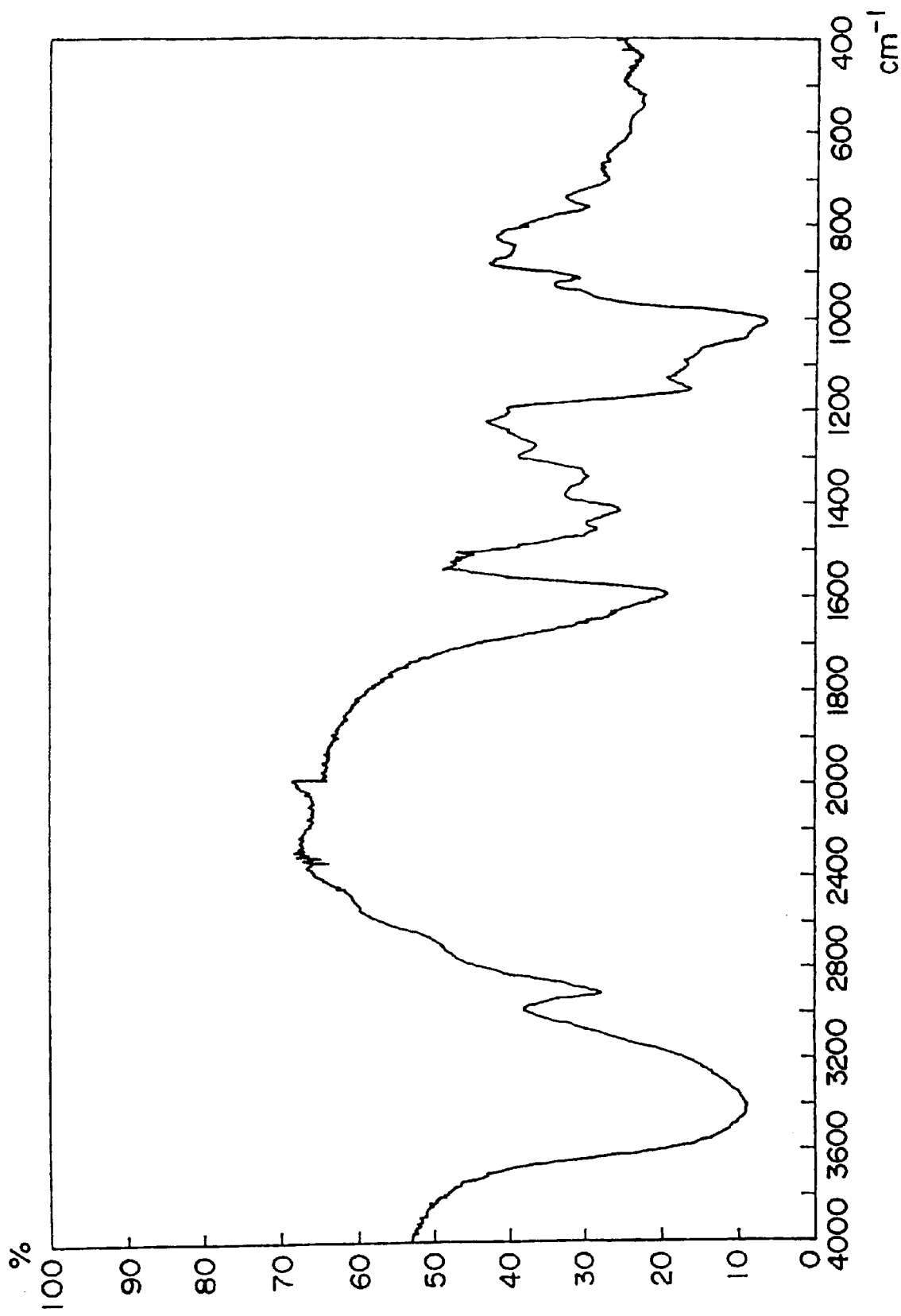
FIG. 2 is the infrared absorption spectral drawing (KBr method) of the polysaccharide derivative No. 8 prepared in Reference Example 2.
Figure 4:
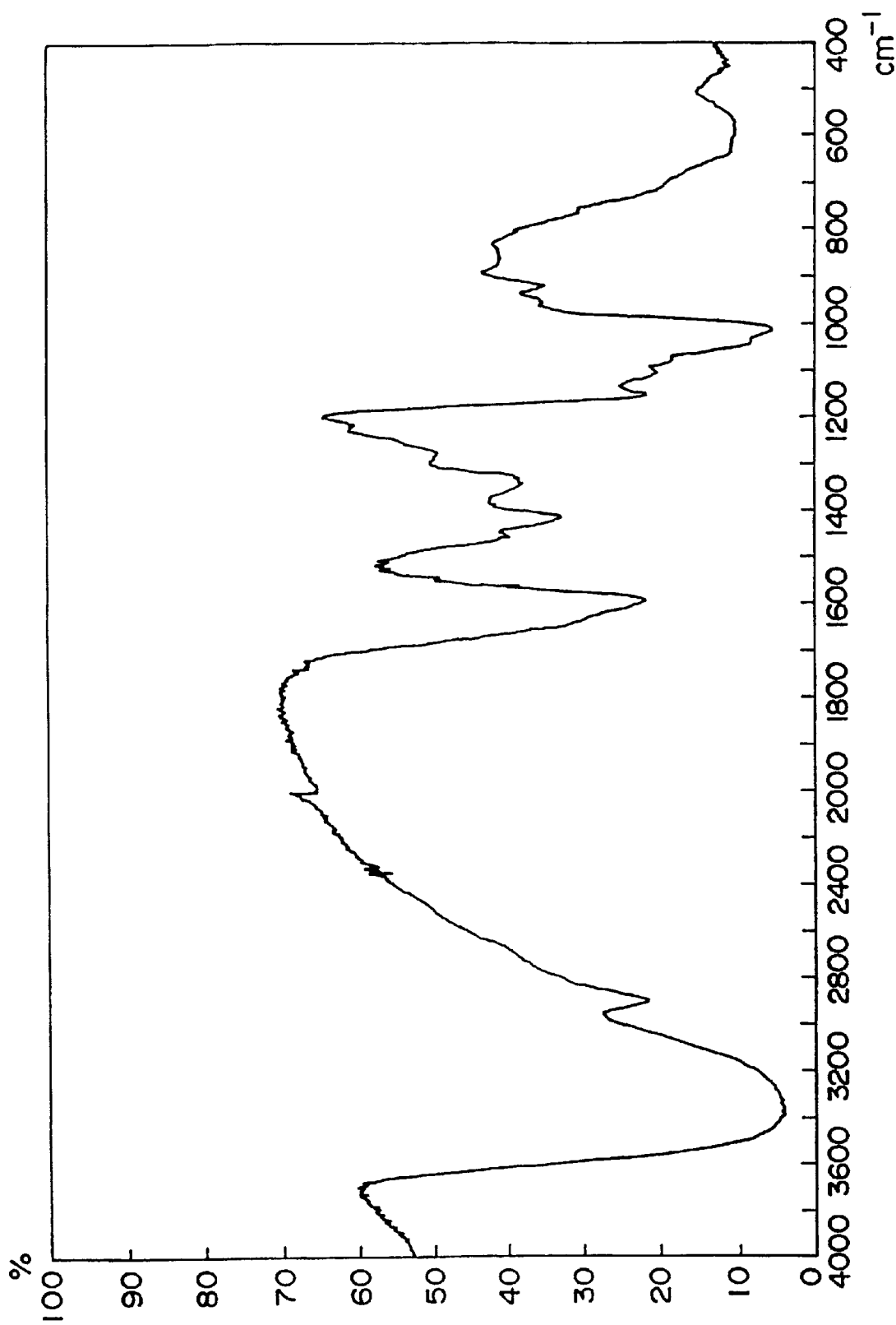
FIG. 4 is the infrared absorption spectral drawing (KBr method) of the freeze-dried powder of the complex No. 6 prepared in Example 1.

The present invention shall more specifically be explained below with reference examples, comparative examples, examples and test examples.

Reference Example 1

Preparation of various polysaccharide carboxymethyl ethers

Various polysaccharides of 500 g are dissolved in water of 1670 ml, and after sodium hydroxide and monochloroacetic acid ($ClCH_2COOH$) are added thereto at about 30° C. or lower, stirring is carried out at about 60° C. for 2 hours. After cooling, the pH is adjusted to 8 with hydrochloric acid, and then 1.5 to 2.5 times as much methanol as the reaction solution volume is added according to the intrinsic viscosities and the substitution rates of carboxymethyl groups (hereinafter abbreviated as a CM group) of the polysaccharides used while stirring to precipitate the intended products. The precipitates are dissolved again in water of 1.5 liter, and the operation for adding methanol to obtain precipitates is repeated further three times. The resultant precipitates are dissolved in water of 1.5 liter, and the pH is adjusted to 8 with sodium hydroxide, followed by filtering with a glass filter, concentrating under reduced pressure and freeze-drying, whereby sodium salts of polysaccharide carboxymethyl ethers (hereinafter referred to as a CM polysaccharide) are obtained. Shown in the following Table 1 are the kinds of the polysaccharides used, the use amounts of sodium hydroxide and monochloroacetic acid which are the raw materials and the yields and the properties of the resultant CM polysaccharides.

TABLE 1

| No. of polysaccharide derivative | Synthesis of CM polysaccharide | | | Yield of CM polysaccharide g | Properties of CM polysaccharide | |
|---|---|---|---|---|---|---|
| | Kind of polysaccharide | Amount of NaOH g | ClCH$_2$COOH g | | Intrinsic viscosity dl/g | CM substitution rate % |
| 2 | Reduced dextran | 67 | 78 | 485 | 0.071 | 2.7 |
| 3 | Reduced dextran | 133 | 157 | 505 | 0.072 | 6.7 |
| 4 | Dextran | 173 | 204 | 553 | 0.075 | 8.3 |
| 5 | Dextran | 173 | 204 | 546 | 0.106 | 8.4 |
| 6 | Pullulan | 173 | 204 | 445 | 0.072 | 8.3 |

Reference Example 2

Preparation of various polysaccharide carboxymethyl diethylaminoethyl ethers

Various CM polysaccharides of 300 g shown in Table 1 are dissolved in water of 900 ml, and after sodium hydroxide and diethylaminoethyl chloride (hereinafter abbreviated as DEAECl) are added thereto at about 30° C. or lower, stirring is carried out at about 60° C. for 2 hours. After cooling, the pH is adjusted to 8 with hydrochloric acid, and then 1.5 to 2.5 times as much methanol and acetone as the reaction solution volume are added according to the molecular weights (intrinsic viscosities) and the substitution rates of the diethylaminoethyl groups (hereinafter abbreviated as an EA group) of the polysaccharides used while stirring to precipitate the intended products. The precipitates are dissolved again in water of 1.5 liter, and the operation for adding methanol and acetone to obtain precipitates is repeated further three times. The resultant precipitates are dissolved in water of 1.5 liter, and the pH is adjusted to 8 with sodium hydroxide, followed by filtering with a glass filter, concentrating under reduced pressure and freeze-drying, whereby sodium and hydrochloric acid salts of polysaccharide carboxymethyl diethylaminoethyl ethers (hereinafter referred to as a CMEA polysaccharide) are obtained. Shown in the following Table 2 are the kinds of the CM polysaccharides used, the use amounts of sodium hydroxide and DEAECl which are the raw materials and the yields and the properties of the resultant CMEA polysaccharides.

about 30° C. or lower, stirring is carried out at about 70° C. for 3 hours. After cooling, the pH is adjusted to 8 with hydrochloric acid, and then about 1.5 times as much methanol as the reaction solution volume is added while stirring to precipitate the intended product. The precipitate is dissolved again in water of 1.5 liter, and the operation for adding methanol to obtain precipitates is repeated further three times. The resultant precipitates are dissolved in water of 1.5 liter, and the pH is adjusted to 8 with sodium hydroxide, followed by concentrating under reduced pressure and freeze-drying, whereby carboxymethyldextran (CMD) is obtained.

Resultant CMD of 300 g is dissolved in water of 400 ml, and after 40% sodium hydroxide of 400 ml and 75% 3-chloro-2-hydroxypropyltrimethylammonium chloride of 925 ml are added thereto at about 30° C. or lower, stirring is carried out at about 65° C. for 2 hours. After cooling, the pH is adjusted to neutrality with hydrochloric acid, and then about 2 times as much methanol as the reaction solution volume is added while stirring to precipitate the intended product. The precipitate is dissolved again in water of 1 liter, and the operation for adding methanol to thereby obtain precipitates is repeated further three times. The resultant precipitates are dissolved in water of 1 liter, and the pH is adjusted to about 7 with sodium hydroxide, followed by filtering with a glass filter, concentrating under reduced pressure and freeze-drying, whereby carboxymethyl trimethylammonio-2-hydroxypropyldextran (polysaccharide derivative No. 14) of 285 g is obtained. Intrinsic viscosity: 0.15 dl/g, CM substitution rate: 14%, trimethylammonio-2-hydroxypropyl substitution rate: 14%.

TABLE 2

| No. of polysaccharide derivative | Synthesis of CMEA polysaccharide | | | Yield of CMEA polysaccharide g | Properties of CMEA polysaccharide | | |
|---|---|---|---|---|---|---|---|
| | Kind of CM polysaccharide | Amount of NaOH g | DEAECl g | | Intrinsic viscosity dl/g | CM substitution rate % | EA substitution rate % |
| 7 | 2 | 23 | 48 | 305 | 0.072 | 2.7 | 4.3 |
| 8 | 3 | 45 | 96 | 314 | 0.073 | 6.7 | 7.0 |
| 9 | 4 | 23 | 48 | 308 | 0.076 | 8.3 | 3.3 |
| 10 | 4 | 59 | 128 | 336 | 0.076 | 8.3 | 7.7 |
| 11 | 4 | 104 | 225 | 280 | 0.076 | 8.3 | 12.4 |
| 12 | 5 | 60 | 127 | 270 | 0.11 | 8.4 | 8.6 |
| 13 | 6 | 60 | 127 | 305 | 0.073 | 8.3 | 10.2 |

Reference Example 3

Preparation of carboxymethyl trimethylammonio-2-hydroxypropyldextran

Dextran of 500 g is dissolved in water of 1200 ml, and after 40% sodium hydroxide of 540 ml and monochloroacetic acid (ClCH$_2$COOH) of 252 g are added thereto at Comparative Example 1

Modified dextran (intrinsic viscosity=0.070 dl/g; hereinafter abbreviated as CDx) of 86 g is dissolved in water of 240 ml, and a mixed iron salt solution obtained by dissolving ferrous chloride tetrahydrate of 18 g in a 1M ferric chloride solution of 184 ml is added thereto while substituting with nitrogen and heating at about 80° C. under stirring. Further, a 3N sodium hydroxide aqueous solution is added to about pH 11. Next, hydrochloric acid is added to adjust the pH to 7, and then the solution is refluxed by heating for one hour. After cooling, the solution is centrifuged, and an about 0.9 time amount of methanol is added to the supernatant to precipitate preferentially a complex.

The resultant precipitate is dissolved in water, and the solution is subjected to water flow dialysis for one night. The dialyzed solution is adjusted to pH 8 and concentrated under reduced pressure. Next, the solution is filtered by a membrane filter (pore size: 0.45 µm) and then charged into an ampul (Complex No. 1). Iron content: 56 mg/ml, iron yield: 88%, sugar content:

66 mg/ml, core diameter: 7.7 nm, T1 relaxibity (hereinafter abbreviated as T1-R): 44 $(mM \cdot sec)^{-1}$, and T2 relaxibity (hereinafter abbreviated as T2-R): 209 $(mM \cdot sec)^{-1}$.

Comparative Example 2

Respective polysaccharide derivatives (CM polysaccharides) 86 g of No. 2, 3 and 4 prepared in Reference Example I are dissolved in water of 240 ml respectively, and a mixed iron salt solution obtained by dissolving ferrous chloride tetrahydrate of 18 g in a 1M ferric chloride solution of 184 ml is added thereto while substituting with nitrogen and heating at about 80° C. under stirring. Further, a 3N sodium hydroxide aqueous solution is added to about pH 11. Next, hydrochloric acid is added to adjust the pH to 7, and then the solution is refluxed by heating for one hour. After cooling, the solution is centrifuged, and an about 0.5 to about 0.8 time amount of methanol is added to the supernatant according to the substitution rates of the CM polysaccharides used to precipitate preferentially a complex. The resultant precipitate is dissolved in water, and the solution is subjected to water flow dialysis for one night. The dialyzed solution is adjusted to pH 8 and concentrated under reduced pressure. Next, the solution is filtered by a membrane filter (pore size: 0.45 µm) and then charged into an ampul (Complexes No. 2, 3 and 4). The properties of the resultant complexes are shown in the following Table 3.

TABLE 3

| No. of Complex | No. of polysaccharide used | Iron content mg/ml | Yield % | Content of polysaccharide mg/ml | Core diameter nm | T1-R 1/mM · sec | T2-R 1/mM · sec |
|---|---|---|---|---|---|---|---|
| 2 | 2 | 55 | 85 | 63 | 7.3 | 24 | 103 |
| 3 | 3 | 52 | 87 | 59 | 6.5 | 31 | 96 |
| 4 | 4 | 53 | 82 | 82 | 6.8 | 33 | 98 |

Example 1

Respective polysaccharide derivatives (CMEA polysaccharides) of No. 7 to 13 prepared in Reference Example 2 are dissolved in water of 240 ml respectively, and a mixed iron salt solution obtained by dissolving ferrous chloride tetrahydrate of 18 g in a 1M ferric chloride solution of 184 ml is added thereto while substituting with nitrogen and heating at about 80° C. under stirring. Further, a 3N sodium hydroxide aqueous solution is added to about pH 11. Next, hydrochloric acid is added to adjust the pH to 7, and then the solution is refluxed by heating for one hour. After cooling, the solution is centrifuged, and an about 0.5 to about 0.8 time amount of methanol is added to the supernatant according to the substitution rates and the molecular weights of the CMEA polysaccharides used to precipitate preferentially a complex. The resultant precipitate is dissolved in water, and the solution is subjected to water flow dialysis for one night. The dialyzed solution is adjusted to pH 8 and concentrated under reduced pressure. Next, the solution is filtered by a membrane filter (pore size: 0.45 to 10 µm) and then charged into an ampul (Complexes No. 5 to 10). The properties of the resultant complexes are shown in the following Table 4.

TABLE 4

| No. of Complex | No. of polysaccharide used | Iron content mg/ml | Yield % | Content of polysaccharide mg/ml | Core diameter nm | T1-R 1/mM · sec | T2-R 1/mM · sec |
|---|---|---|---|---|---|---|---|
| 5 | 7 | 45 | 90 | 96 | 7.1 | 27 | 103 |
| 6 | 8 | 52 | 88 | 128 | 6.2 | 19 | 68 |
| 7 | 9 | 37 | 80 | 90 | 5.4 | 25 | 226 |
| 8 | 10 | 54 | 91 | 122 | 5.8 | 23 | 249 |
| 9 | 12 | 56 | 87 | 273 | 6.4 | 30 | 83 |
| 10 | 13 | 44 | 77 | 68 | 5.8 | 30 | 133 |

Example 2

A polysaccharide derivative 86 g of No. 14 prepared in Reference Example 3 is dissolved in water of 300 ml, and a mixed iron salt solution obtained by dissolving ferrous chloride tetrahydrate of 18 g in a 1M ferric chloride solution of 184 ml is added thereto while substituting with nitrogen and heating at about 80° C. under stirring. Further, a 3N sodium hydroxide aqueous solution is added to about pH 11. Next, hydrochloric acid is added to adjust the pH to 7, and then the solution is refluxed by heating for one hour. After cooling, the solution is centrifuged, and an about 1.5 time amount of methanol is added to the supernatant to precipitate preferentially a complex. The resultant precipitate is dissolved in water, and the solution is subjected to water flow dialysis for one night. The dialyzed solution is adjusted to pH 8 and concentrated under reduced pressure. Next, the solution is filtered and then charged into an ampul (Complex No. 11). Iron content: 12 mg/ml, iron yield: 18%, sugar content: 76 mg/ml, and core diameter: 6.5 nm.

Test Example 1

Safety test

The acute toxicities ($LD_{50}$) of the respective complexes prepared in Comparative Examples 1 and 2 and Examples 1 and 2 were determined. The aqueous sols of the respective complexes were intravenously administered to a group/five mice of five-week-old dd-strain (male) in amounts of 10, 20, 40, 80 and 160 mmol/kg in terms of iron, and life or death thereof was observed for one week to calculate the $LD_{50}$ values according to the Behrens Karber method. The $LD_{50}$ values of the respective complexes are shown in the following Table 5.

TABLE 5

| No. of Complex | LD$_{50}$ (mmol (Fe)/kg) | No. of Complex | LD$_{50}$ (mmol (Fe)/kg) |
| --- | --- | --- | --- |
| 1 | 25 | 5 | 60 |
| 2 | 100 | 6 | 40 |
| 3 | 70 | 8 | 30 |
| 4 | 80 | 11 | 30 |

Test Example 2

Blood clearance test

The blood clearances (rates at which the complexes are removed from blood) of the respective complexes prepared in Comparative Examples 1 and 2 and Example 1 were determined in terms of a half life. The aqueous sols of the respective complexes were intravenously administered to a group/2 to 3 rats of six to seven-week-old Wister-strain in an amount of each 2.5 mg/kg in terms of iron, and the bloods of the rats were sampled and the organs thereof were taken out at 4 to 8 points with the lapse of time. T1 and T2 relaxation times of the whole bloods sampled and the blood plasmas obtained by subjecting the whole bloods to centrifugal treatment were measured. The half life of the blood clearance was calculated from the relation of the elapsing time from administration to blood sampling with a reciprocal number of T1 or T2 relaxation time. Almost the same half lives were calculated for either of the whole bloods and the blood plasmas in the both case of the T1 and T2 relaxation times. The results obtained are shown in the following Table 6.

TABLE 6

| No. of complex | Half life | No. of complex | Half life |
| --- | --- | --- | --- |
| 1 | 0.9 hour | 5 | 6.1 hours |
| 2 | 1.4 hours | 6 | 6.8 hours |
| 3 | 1.6 hours | 7 | 9 minutes |

We claim:

1. A complex of a magnetic metal oxide and a polysaccharide derivative, wherein the derivative is obtained by carboxyalkyl-etherifying and aminoalkyl-etherifying a polysaccharide, where the aminoalkyl is optionally substituted.

2. The complex as described in claim 1, wherein the polysaccharide is dextran, starch, cellulose or pullulan.

3. The complex as described in claim 1, wherein the polysaccharide is dextran.

4. The complex as described in claim 1, wherein the carboxyalkyl ether part of the polysaccharide derivative is carboxymethyl ether, carboxyethyl ether or carboxypropyl ether.

5. The complex as described in claim 1, wherein the unsubstituted or substituted aminoalkyl ether part of the polysaccharide derivative is represented by the following formula:

(III-1)

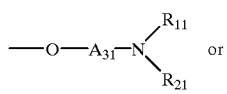

or

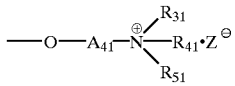

(IV-1)

wherein $A_{31}$ and $A_{41}$ each represent an alkylene group which may be substituted with a hydroxy group;

$R_{11}$ and $R_{21}$ represent independently a hydrogen atom or a lower alkyl group, or $R_{11}$ and $R_{21}$ are combined with a nitrogen atom to which they are bonded to form a 5- or 6-membered nitrogen-containing heterocyclic;

$R_{31}$, $R_{41}$ and $R_{51}$ represent independently a hydrogen atom or a lower alkyl group or at least two of $R_{31}$, $R_{41}$ and $R_{51}$ are combined with a nitrogen atom to which they are bonded to form a 5- or 6-membered nitrogen-containing heterocyclic; and Z represents an anion.

6. The complex as described in claim 1, wherein the polysaccharide derivative has an intrinsic viscosity falling in the range of about 0.02 to about 0.5 dl/g.

7. The complex as described in claim 1, wherein a carboxyalkyl group and an unsubstituted or substituted aminoalkyl group in the polysaccharide derivative have substitution rates falling in the ranges of about 1 to about 30%.

8. The complex as described in claim 1, wherein the magnetic metal oxide has a diameter falling in the range of about 2 to 20 nm.

9. The complex as described in claim 1, wherein the magnetic metal oxide is represented by the following formula:

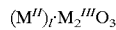

wherein $M^{II}$ represents a divalent metal atom;

$M^{III}$ represents a trivalent metal atom; and l is a real number falling in the range of 0 to 1.

10. The complex as described in claim 9, wherein the magnetic metal oxide is represented by the following formula:

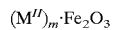

wherein $M^{II}$ represents a divalent metal atom, and m is a real number falling in the range of 0 to 1.

11. The complex as described in claim 10, wherein the magnetic metal oxide is represented by the following formula:

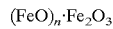

wherein n is a real number falling in the range of 0 to 1.

12. The complex as described in claim 1, containing the polysaccharide derivative in the range of 0.2 to 10 parts by weight per part by weight of metal contained in the magnetic metal oxide.

13. The complex as described in claim 10, wherein the diameter measured by a light scattering method falls in the range of about 10 to about 500 nm.

14. A method for producing the complex according to any of claims 1 to 13, which comprises:

(a) reacting an aqueous sol containing magnetic metal oxide particles with a polysaccharide derivative obtained by carboxyalkyl-etherifying and aminoalkyl-etherifying a polysaccharide, wherein the aminoalkyl is optionally substituted, or (b) reacting a mixture of a water-soluble salt of a divalent metal and a water-soluble salt of a trivalent metal with a base in an aqueous medium in the presence of the polysaccharide derivative.

15. An MRI contrast medium comprising the complex described in any of claims 1 to 13.

16. The MRI contrast medium as described in claim 15, which is an MRI contrast medium for blood vessel or lymph node.

17. The MRI contrast medium as described in claim 15, which is an MRI contrast medium for tumor or cancer site.

18. The complex according to claim 1, wherein at least one of the carboxy group and amino group is present as a salt form in the molecule.

19. The complex according to claim 1, wherein the polysaccharide derivative has an intrinsic viscosity falling in the range of about 0.04 to about 0.2 dl/g.

20. The complex according to claim 1, wherein a carboxyalkyl group and an unsubstituted or substituted aminoalkyl group in the polysaccharide derivative have substitution rates falling in the range of about 2 to 16%.

21. The complex as described in claim 1, wherein the magnetic metal oxide has a diameter falling in the range of about 3 to 15 nm.

* * * * *